United States Patent
Huang et al.

(10) Patent No.: US 12,427,274 B2
(45) Date of Patent: Sep. 30, 2025

(54) METHODS FOR CAPTURING RESPIRATORY DROPLETS

(71) Applicant: Northwestern University, Evanston, IL (US)

(72) Inventors: Jiaxing Huang, Wilmette, IL (US); Murat Kadir, Broadview Heights, OH (US); Zhilong Yu, Evanston, IL (US)

(73) Assignee: Northwestern University, Evanston, IL (US)

( * ) Notice: Subject to any disclaimer, the term of this patent is extended or adjusted under 35 U.S.C. 154(b) by 855 days.

(21) Appl. No.: 17/708,232

(22) Filed: Mar. 30, 2022

(65) Prior Publication Data

US 2022/0313931 A1 Oct. 6, 2022

Related U.S. Application Data

(60) Provisional application No. 63/168,889, filed on Mar. 31, 2021.

(51) Int. Cl.
  *F24F 8/00* (2021.01)
  *A61M 16/00* (2006.01)
  *F24F 8/10* (2021.01)

(52) U.S. Cl.
  CPC ............ *A61M 16/0093* (2014.02); *F24F 8/10* (2021.01); *A61L 2209/14* (2013.01); *B01D 2257/91* (2013.01)

(58) Field of Classification Search
  CPC ... A61M 16/0093; F24F 8/10; A61L 2209/14; B01D 2257/91; C09D 5/14; C09D 133/02
  USPC .......................................................... 510/259
  See application file for complete search history.

(56) References Cited

U.S. PATENT DOCUMENTS

2007/0298086 A1\* 12/2007 Deal ...................... A61J 19/00
424/443
2019/0000745 A1\* 1/2019 Chiattello ............ A61K 8/8158

OTHER PUBLICATIONS

M. Damak, M. N. Hyder, K. K. Varanasi, Enhancing droplet deposition through in-situ precipitation. *Nat. Commun.* 7, 12560 (2016).
J. Haldar, A. K. Weight, A. M. Klibanov, Preparation, application and testing of permanent antibacterial and antiviral coatings. *Nat. Protoc.* 2, 2412 (2007).
L. Richter, M. Hijazi, F. Arfeen, C. Krumm, J. C. Tiller, Telechelic, Antimicrobial Hydrophilic Polycations with Two Modes of Action. *Macromol. Biosci.* 18, 1700389 (2018).
H. Li et al., Spontaneous droplets gyrating via asymmetric self-splitting on heterogeneous surfaces. *Nat. Commun.* 10, 950 (2019).
M. R. Song et al., Controlling liquid splash on superhydrophobic surfaces by a vesicle surfactant. *Sci. Adv.* 3, (2017).

(Continued)

*Primary Examiner* — Eisa B Elhilo
(74) *Attorney, Agent, or Firm* — Bell & Manning, LLC

(57) ABSTRACT

Methods of capturing respiratory droplets are provided which use coatings comprising a polyelectrolyte polymer and a viscosity modifier. In embodiments, a method of capturing respiratory droplets comprises absorbing respiratory droplets on a surface of a coating, the coating comprising a polyelectrolyte polymer and a viscosity modifier, wherein absorbed droplets leave depressions in the surface of the coating. Coated substrates and coating compositions used to form the coated substrates are also encompassed.

15 Claims, 14 Drawing Sheets

(56) References Cited

OTHER PUBLICATIONS

M. R. Song et al., Enhancing Droplet Deposition on Wired and Curved Superhydrophobic Leaves. *ACS Nano* 13, 7966 (2019).
V. Bergeron, D. Bonn, J. Y. Martin, L. Vovelle, Controlling droplet deposition with polymer additives. *Nature* 405, 772 (2000).

* cited by examiner

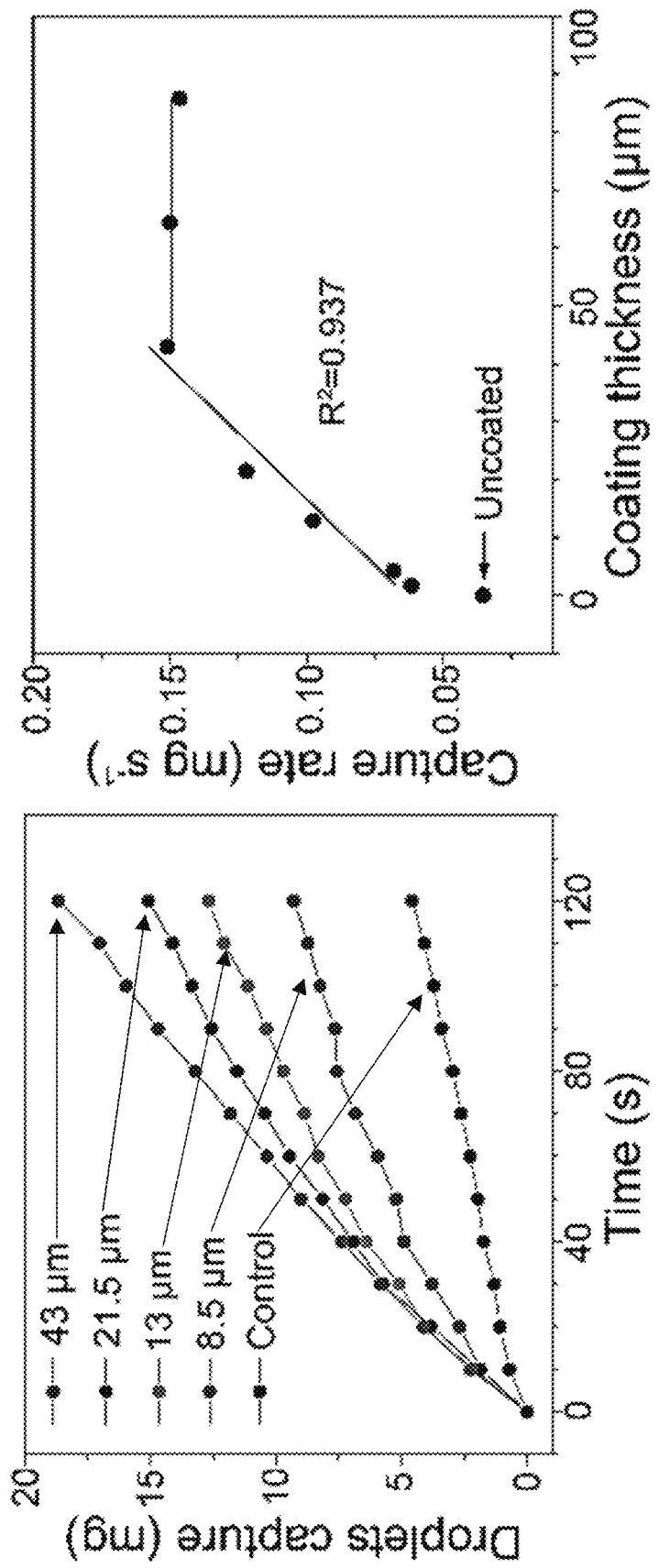

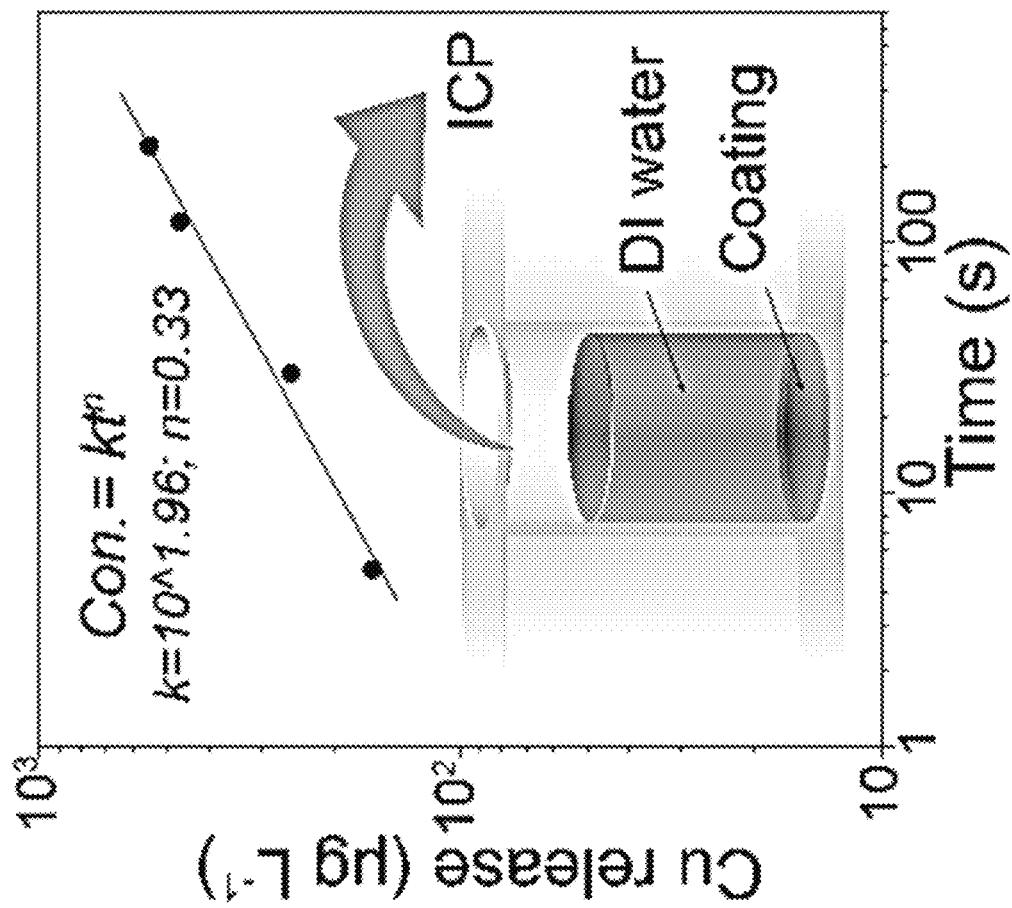

METHODS FOR CAPTURING RESPIRATORY DROPLETS

CROSS-REFERENCE TO RELATED APPLICATIONS

The present application claims priority to U.S. provisional patent application No. 63/168,889 that was filed Mar. 31, 2021, the entire contents of which are incorporated herein by reference.

BACKGROUND

A better understanding of the SARS-CoV-2 virus and the promising development of vaccines has brought a rising sense of optimism of controlling and eventually ending the COVID-19 pandemic. However, infectious respiratory diseases with epidemic and pandemic potential will continue to be a critical global challenge in the future, which requires sustained development of comprehensive preparedness strategies transcending boundaries and scientific disciplines. The chain of transmission starts from pathogen-laden respiratory droplets released in expiratory events such as exhaling, speaking, singing, coughing, and sneezing, which must travel outside human body and endure the surrounding environmental conditions before reaching and eventually infecting others.

SUMMARY

Provided are methods for capturing respiratory droplets, thereby reducing and/or eliminating the transmission of pathogens (e.g., SARS-CoV-2) that may be present within the respiratory droplets. The methods make use of certain coatings. In embodiments, such a method of capturing respiratory droplets comprises absorbing respiratory droplets on a surface of a coating, the coating comprising a polyelectrolyte polymer and a viscosity modifier, wherein absorbed droplets leave depressions in the surface of the coating. Coated substrates and coating compositions used to form the coated substrates are also encompassed.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

FIGS. 1A-1E show that a droplet-capturing surface can remove pathogens from the chain of transmission. FIG. 1A illustrates that physical barriers can divert and diffuse pathogen-laden respiratory droplets towards a susceptible target, reducing the probability of direct infection. However, as droplets bounce or glide off a surface, they re-enter the pathway of air-borne transmission. FIG. 1B shows that a droplet-trapping surface can retain the solutes and dispersants, including any pathogens, effectively removing the pathogens from the chains of transmission. FIG. 1C is a microscopic snapshot of aerosol droplets colliding with a clear PET substrate, taken from behind the substrate under bright-field mode. Most droplets leave a streak corresponding to bouncing or gliding, and only a small fraction is retained. FIG. 1D shows that by contrast, a polyelectrolyte coated PET captures and then absorbs most droplets, eventually leaving crater-like potholes on the polymer coating as shown in the corresponding 3D laser confocal microscopy image (FIG. 1E).

FIGS. 2A-2G demonstrate the enhanced capture of aerosol droplets by a PAAm-DDA coating. FIG. 2A shows how aerosol droplet uptake by a surface can be directly monitored using a balance as illustrated in the drawing. FIG. 2B plots the mass change of glass slides as a function of time, showing that the coated slides gained significantly more mass on exposure to the aerosol stream. FIG. 2C plots capture rate as a function of coating thickness showing that the optimal thickness of the PAAm-DDA coating was found be around 50 µm. FIG. 2D demonstrates the direct visual detection of escaped droplets after an aerosol stream is continuously fed into a 30 cm long PET tube. As illustrated in the drawing, a green laser beam is applied at the exit to detect escaped droplets by scattering. Photos showed that the laser beam at the exit of an uncoated tube was already quite visible about 7 s after the aerosol flow started, and greatly intensified after 30 s. By contrast, photos of a coated PET tube showed that the laser beam was barely visible even after over 60 s. FIGS. 2E-2G show that coated glass traps more aerosol droplets and retains more solid residues but remains haze-free and highly transparent. FIG. 2E plots mass gains of oven-dried glass slides after five rounds of aerosol (10 wt. % NaCl) deposition, showing significantly higher salt (hence droplets) uptake on the polymer coated slide. Photos showed that the uncoated slide became opaque while the coated side remained clear. Microscopy observation under dark field reflectance mode revealed that the (FIG. 2F) uncoated slide is covered by large micron-scale salt crystals, which scatter light strongly. In contrast, similar microscopy observation (FIG. 2G) shows that no large salt crystals can be seen on the coated slide because the droplets were absorbed in the polymer matrix and spread out.

FIGS. 3A-3C demonstrate the tests with speech generated respiratory droplets that were conducted. FIG. 3A is a schematic drawing showing the experimental design, where a droplet collector made of PAAm-DDA-coated silicon wafer (2 cm×2 cm) is placed at the bottom of a Plexiglass® screen (30 cm×60 cm) to collect escaped droplets. FIG. 3B shows that microscopy observation (bright field, reflectance mode) confirms that droplet marks are highly visible for even micron-sized droplets on the optimized collectors. The images also show that there are drastically more droplets escaped from (left) the uncoated screen than from the (right) the coated one. Scale bar: 100 µm. The inset on the left is a higher magnification view. FIG. 3C shows how the droplet-capturing capabilities of (left inset) coated PET face shields (33 cm×27 cm) and (right inset) Plexiglass® screens (30 cm×60 cm) were field-tested with real respiratory droplets released by several volunteers during 30 mins of loud reciting. These respiratory droplets have drastically wider size distribution and orders of magnitude lower flux than those released from an aerosol generator. Here, additional droplet collectors are placed at the external surfaces as a blank control. The number of droplets on the collector was counted for qualitative comparison. Although the flux of droplets released by different persons differs greatly, for each person, both types of coated surfaces drastically cut down escaped droplets to a level comparable to the blank control.

FIGS. 4A-4B demonstrate that droplet-capturing coatings can be applied to common environmental surfaces. FIG. 4A shows a schematic drawing of a workspace having a range of material surfaces (plastics, glass, wood, steel, concrete, and cloth) on which the coatings may be applied so that the surfaces act as droplet-capturing surfaces. To confirm the applicability of the present approach in such a workspace, uniform and conformal coatings were applied to various environmental surfaces of different material compositions, wettability, textures, and geometries, including a Plexiglas® divider screen, a window glass, a complex wood structure, a stainless-steel frame with decorative features, a rough concrete wall, and a microfiber cloth curtain, all of which are common indoor surfaces in medical, work, and public settings. The coatings were arbitrarily colored with dyes to make them distinguishable from the surfaces. FIG. 4B shows that common disinfectants such as $Cu^{2+}$ can be incorporated in the coatings and released in the presence of water (following Fick's diffusion law) for disinfection purposes.

DETAILED DESCRIPTION

Figure 1A:
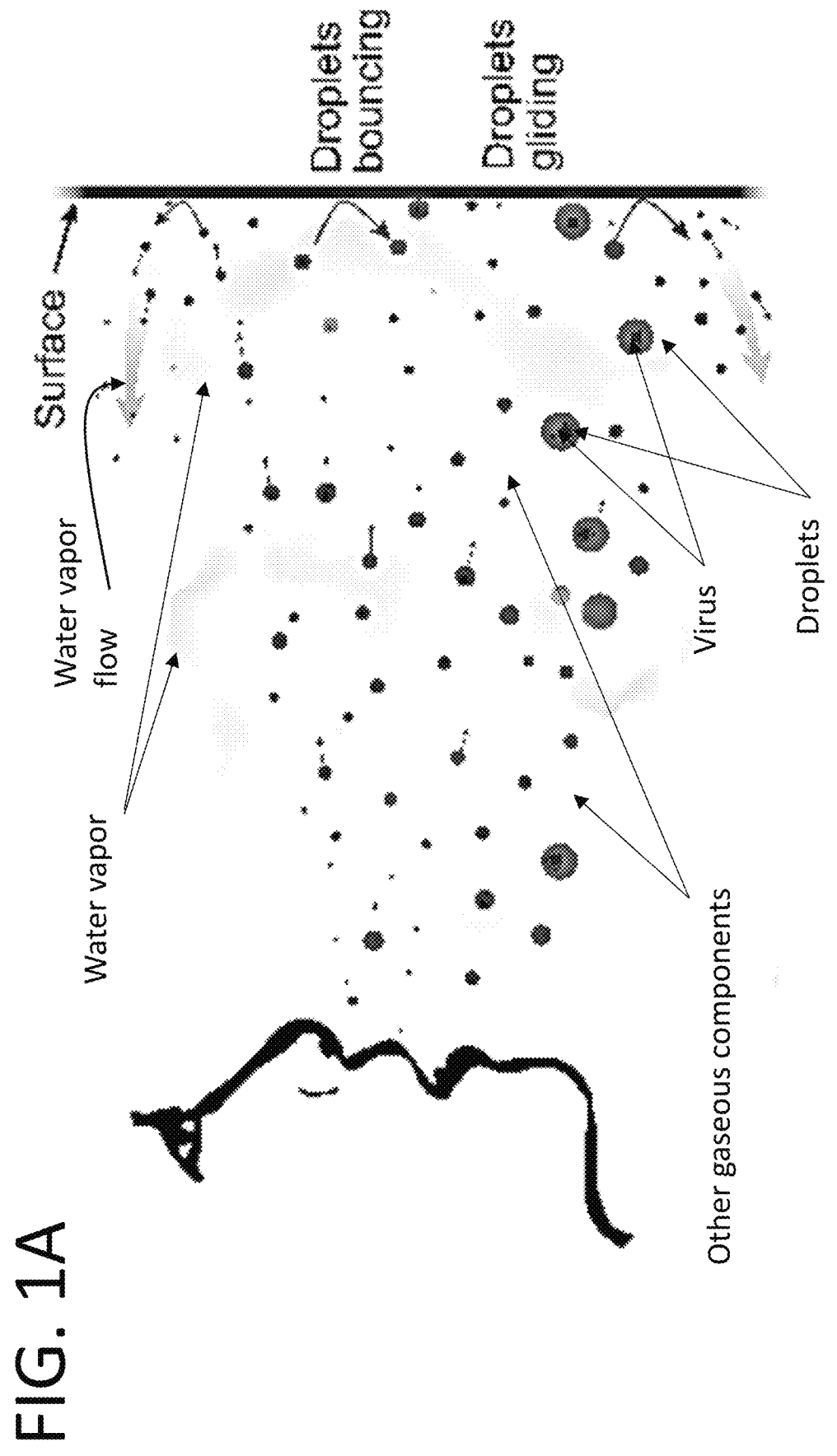
Figure 1B:
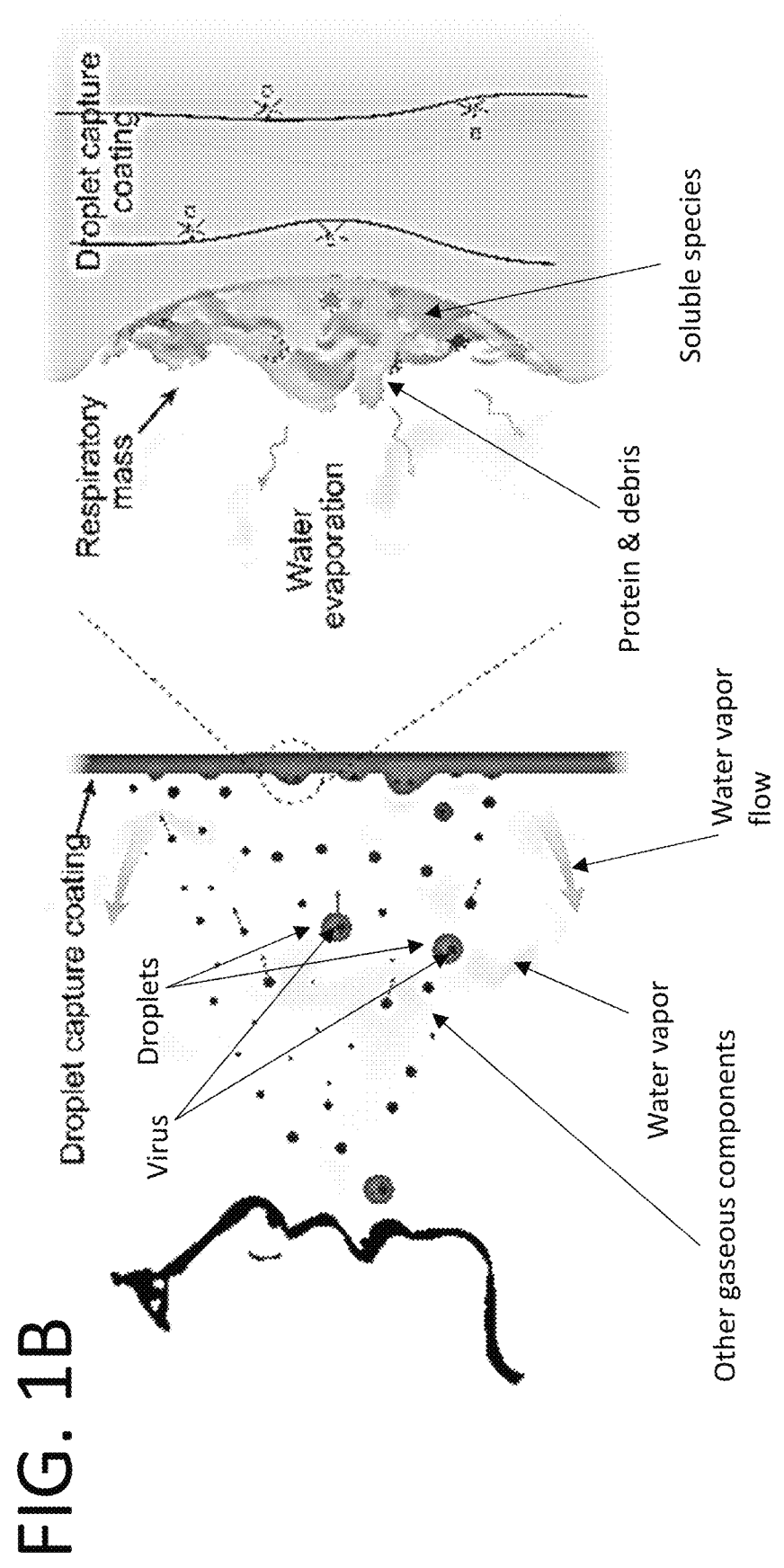
Figure 1C:
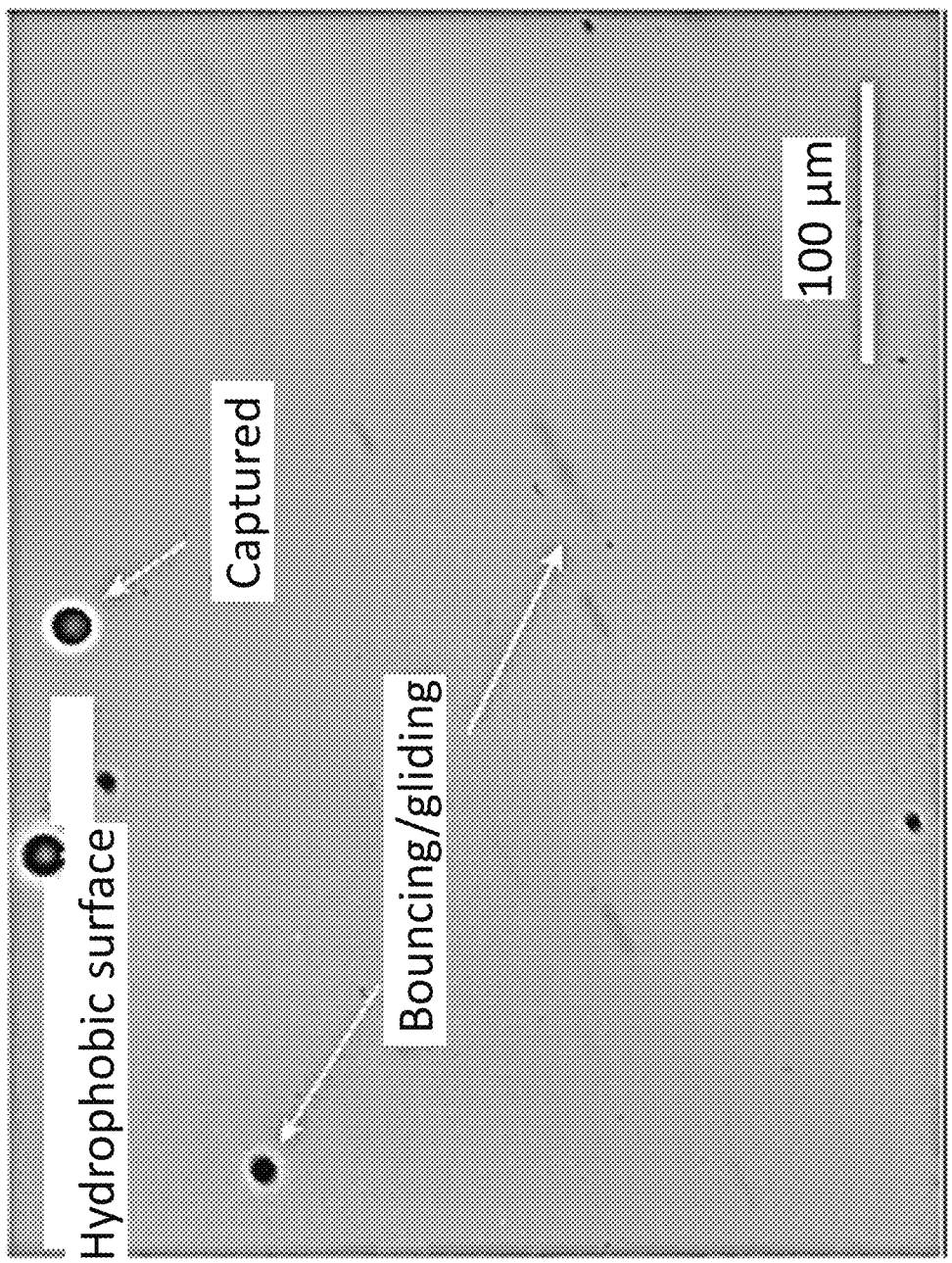
Figure 1D:
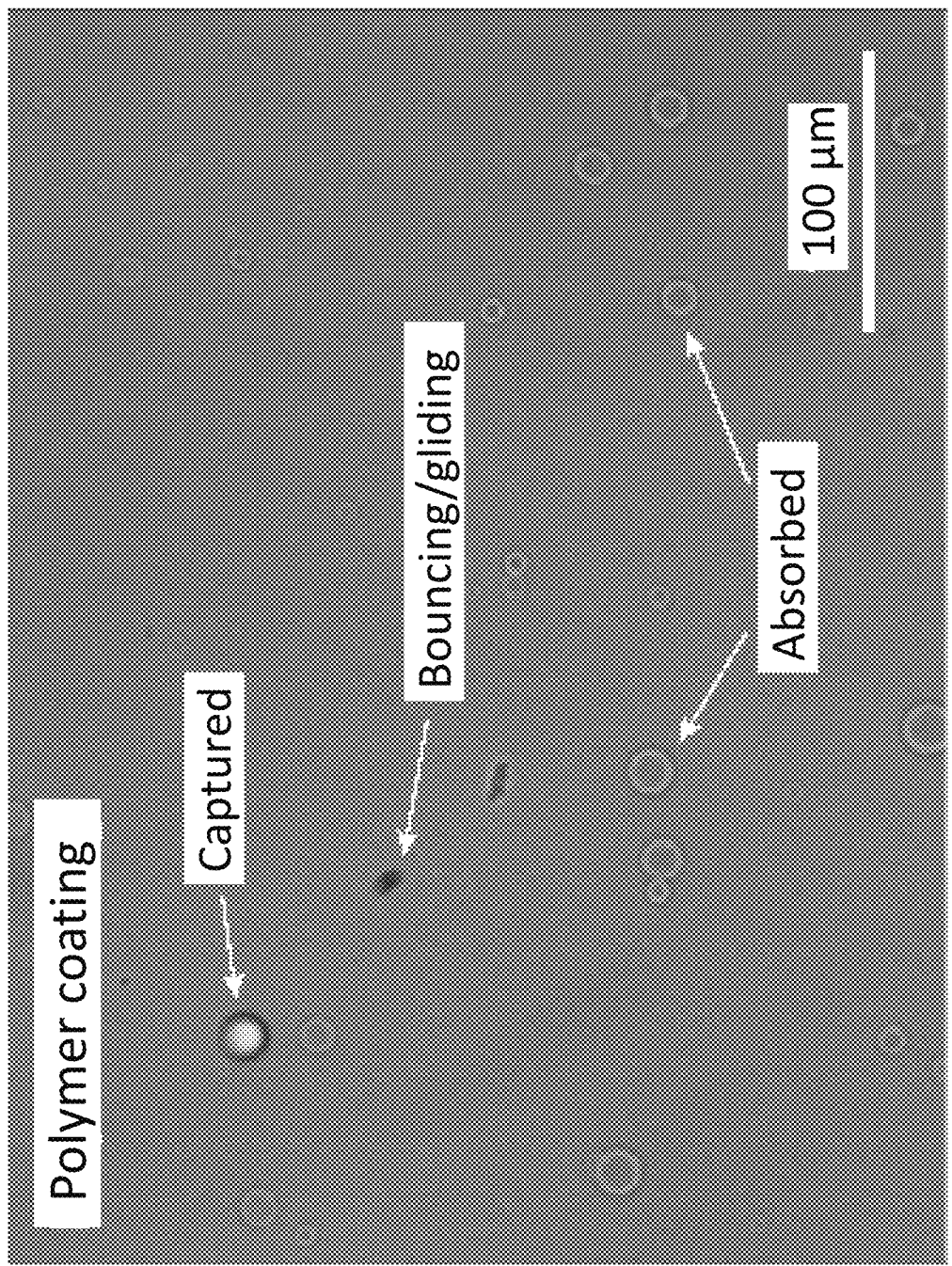
Figure 1E:
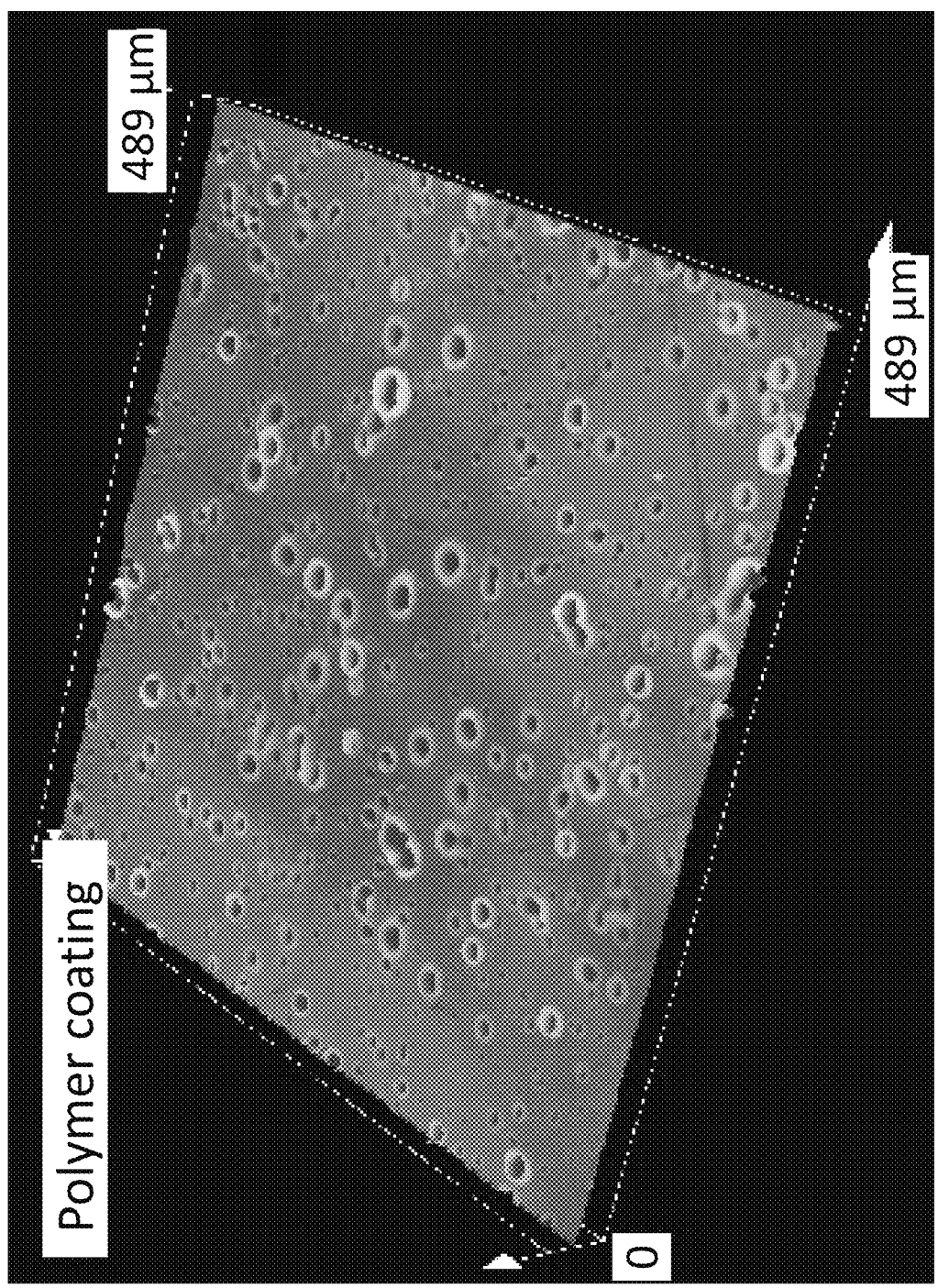

In one aspect, the present disclosure provides methods of capturing respiratory droplets. The capture of respiratory droplets out of the atmosphere in which they are present interferes with the transmission path of pathogens that may be present within the droplets. In an embodiment, such a method comprises absorbing the respiratory droplets on a surface of a coating, the coating comprising a hydrophilic polymer and a viscosity modifier. The respiratory droplets may be those exhaled from the breath of a mammalian subject (e.g., a human) and as such, comprise water. Due to water evaporation and/or diffusion of water into the coating, the absorbed respiratory droplets leave depressions in the surface of the coating which are readily visualized, e.g., via microscopic images. (See FIGS. 1A, 1B, and 1E.) The size and shape of these depressions is related to the size and shape of the respiratory droplets (as well as the velocity and angle of impact of the respiratory droplets). However, as shown in FIG. 1E, the depressions generally have a circular outline and a diameter on the order of a few to tens of microns. In the absence of the present coatings, exhaled respiratory droplets may interact with a variety of surfaces (e.g., by striking, bouncing off, gliding across), but are not absorbed by such surfaces, nor do they generate the depressions referenced above. (See FIG. 1C). By contrast, the present coatings are capable of capturing a significant number of respiratory droplets out of the surrounding atmosphere due to their particular compositions, thicknesses, etc., as further described below.

Confirmation that the present coatings capture/absorb respiratory droplets may be carried out using the techniques described in the Example, below. Briefly, a balance may be used to measure the mass increase of the coating over time in the presence of a source of respiratory droplets. (See FIGS. 2A, 2B, 2C.) This technique may also be used to quantify a capture rate for the coating. In embodiments, the capture rate is at least $10^2$ mg/m² h, at least $10^3$ mg/m² h, at least $10^4$ mg/m² h, at least at least $10^5$ mg/m² h, or at least at least $10^6$ mg/m² h. This includes a capture rate in a range of from 10 mg/m² h to $10^6$ mg/m² h or $10^2$ mg/m² h to $10^5$ mg/m² h.

These capture rates may be associated with a particular coating thickness, the value of which is measured across opposing surfaces of the coating in a direction normal to the plane of the coating. In embodiments, the thickness is at least 5 μm, at least 10 μm, at least 25 μm, at least 50 μm, or in a range of from 1 μm to 100 μm. As shown in FIG. 2C, the inventors have also determined that the present coatings generally exhibit a thickness value at which the capture rate of the coating is both stable and maximized. That is, at this thickness value, the capture rate of the coating is at its highest value and does not change with greater thicknesses (e.g., is within ±10%, ±5%, or ±2% of the highest value). By way of illustration, FIG. 2C shows that the capture rate of the measured coating is stable and maximized at a thickness value of about 50 μm. In embodiments, the thickness value at which the capture rate is stable and maximized is in a range of from 25 μm to 75 μm or from 30 μm to 60 μm.

Figure 5:
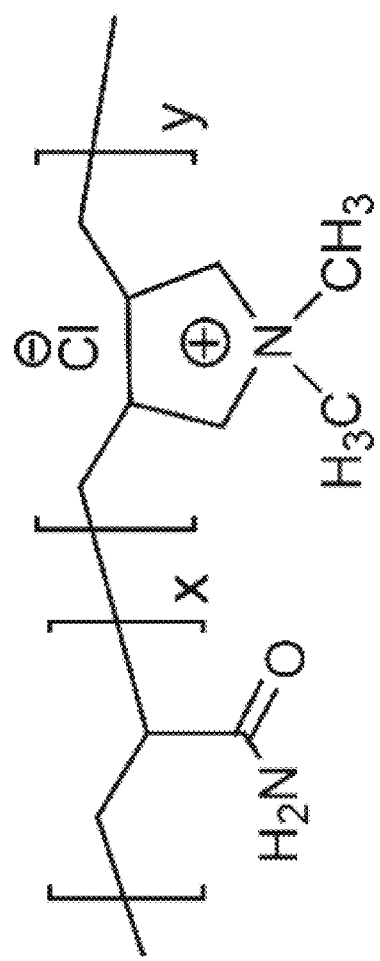
FIG. 5 shows the structure of a polyelectrolyte polymer that may be used in the present coatings, containing acrylamide and quaternary ammonium salt segments.

As noted above, the present coatings comprise a hydrophilic polymer and a viscosity modifier. A variety of hydrophilic polymers may be used, provided the polymer comprises functional groups capable of associating with water, e.g., via hydrogen bonds. Ionic groups are such functional groups. Thus, in embodiments, the hydrophilic polymer is a polyelectrolyte polymer. Suitable polyelectrolyte polymers include polydiallyldialkylammonium salts. Poly(acrylamide-co-diallyldialkylammonium salts) such as the one shown in FIG. 5. are particularly useful. Suitable viscosity modifiers include nonionic surfactants such as alkyl polyglycosides. Combinations of different polyelectrolyte polymers and viscosity modifiers may be used.

The relative amounts of the hydrophilic polymer and the viscosity modifier may be selected to facilitate formation of the coating on the desired substrate. In embodiments, the weight ratio of hydrophilic polymer (e.g., polyelectrolyte polymer):viscosity modifier is in a range of from 5:1 to 1:1. This includes from 4:1 to 2:1 and from 3:1 to 2:1.

The present coatings are formed from coating compositions which also comprise the hydrophilic polymer and viscosity modifier. However, the coating compositions further comprise one or more solvents selected to dissolve the hydrophilic polymer and viscosity modifier. Suitable solvents include water and a variety of alcohols, e.g., methanol, ethanol, isopropanol. Although the solvent(s) may evaporate after application of the coating composition on the desired substrate, some amount of any of these solvent(s) may remain in the present coatings.

The present coatings may also comprise other additives by including them in the coating compositions. Illustrative additives include colorants (e.g., pigments, dyes, etc.) and anti-pathogen agents. Broad spectrum anti-pathogen agents may be used, such as copper salts to provide $Cu^{2+}$ ions in the coatings.

Various amounts of the solvent(s) and additive(s) may be used to achieve the desired effect (e.g., dissolution of hydrophilic polymer/viscosity modifier, color, anti-pathogen activity). Illustrative embodiments include coating compositions comprising from 1 weight % to 10 weight % hydrophilic polymer, from 1 weight % to 5 weight % viscosity modifier, from 0 weight % to 1 weight % additive, with the balance made up of the solvent(s).

In embodiments, the present coating consists of one or more of any of the disclosed hydrophilic polymers, one or more of any of the disclosed viscosity modifiers, and optionally, one or more of the disclosed additives. However, an amount of water may be present in such coatings due to the hydrophilic nature of the hydrophilic polymer. In embodiments, the coating composition consists of one or more of any of the disclosed hydrophilic polymers, one or more of any of the disclosed viscosity modifiers, one or more of the disclosed solvents, and optionally, one or more of the disclosed additives.

To form the coatings and coated substrates used in the present methods, any of the disclosed coating compositions are applied onto the desired substrate. The coating compositions may be applied by a variety of techniques such as dipping, spraying, brushing, painting, spinning, spreading, etc. An advantage of the present coatings is that they are "surface agnostic," by which it is meant the coating compositions may be applied to a wide variety of substrates and transform the surfaces of such substrates into droplet capturing surfaces. Illustrative substrates include those composed of materials such as glass, plastic, wood, metal, steel, concrete, cloth, etc. These substrates may be components or parts of components found in a variety of environments such as offices, schools, stores, schools, hospitals, etc.

An additional advantage of the present coatings is that they remain haze free, even after repeated use. (See FIGS. 2E and 2G.) The anti-haze nature of the coatings may be quantified by the percent transmission of light therethrough. In embodiments, the coating is characterized by a transmission of at least 85%, at least 90%, at least 95%, or at least 99%. The light being transmitted may be white light. These transmission values may be those which are obtained after a specific quantity of respiratory droplets have been captured by the coating, e.g., 20 mg, 50 mg, 100 mg, etc.

The present methods of capturing respiratory droplets may comprise additional steps, including one or more of forming any of the disclosed coatings on a substrate; forming any of the disclosed coating compositions; and exposing any of the disclosed coatings/coated substrates to the respiratory droplets. The exposing step may be performed, e.g., by placing any of the disclosed coatings in an atmosphere comprising exhaled respiratory droplets or in the path of exhaled respiratory droplets. In addition, because the present coatings are not covalently bound to their underlying substrates, they are easily removed therefrom. Thus, an additional step of the present methods may include removing any of the disclosed coatings from an underlying substrate. Finally, as noted above, the coating compositions, coatings, and coated substrates are also encompassed by the present disclosure.

EXAMPLE

Introduction

Transmission of infectious respiratory diseases starts with pathogen-laden respiratory droplets released from a source. Here, a surface-agnostic, polymer-based coating is demonstrated that significantly enhances the capture of lab-generated aerosols and real respiratory droplets. The water-based formulation contains only cosmetic ingredients, and yields uniform, conformal, and non-destructive coatings on a broad range of indoor environmental surfaces regardless of the material composition, wettability, and texture. The coating remains transparent and haze-free even after extensive droplet deposition. Additives can be readily incorporated to bring additional functions, including coloration and sanitization. The strategy repurposes large areas of barely touched indoor environmental surfaces for droplet removal and eliminates these infectious sources from the chain of transmission, which should help to prevent or slow down the overall spread of the pathogens.

Experimental

Materials and Methods

All chemicals were purchased from Sigma-Aldrich and used as-received. All the aerosols were generated by a handheld VP-M3A micro-mesh nebulizer (Xiaomi Inc.). Optical microscopy observations were made on a Nikon TE2000-U inverted microscope and images were taken with a monochrome interline CCD camera (Photometrics, Cool-SNAP HQ2). 3D surface imaging was acquired with an Olympus 3D Laser Confocal Microscope. Viscosities of the polymer solutions and the formulated gel were measured by a Viscolead Adv instrument with spindles. Coated silicon (Si) wafers were prepared by using spin-coating with a Laurell WS-400-6NPP-LITE spin coater. UV/vis spectra were taken with an Agilent 8453 UV/Vis spectrometer. Elemental analysis was conducted on a Thermo iCAP Q (ICP-MS).

Formulation and coating. The main ingredient is polyelectrolyte PAAm-DDA. The PAAm-DDA came as a viscous 10 wt. % aqueous solution. For the polymer coating on the glass slide, the solution was blade-coated on glass slides with gaps of 50-1000 μm. To make sure the coating solution was compatible with different surfaces (e.g hydrophobic surfaces), 2 wt. % cosmetic-grade non-ionic surfactant alkyl polyglycosides (APG) was added to 5 wt. % PAAm-DDA solution. Deionized water (DIW)-alcohol (25 wt %) mixture was used as a solvent to suppress air bubble formation and accelerate drying. Finally, after thoroughly spin-mixing the ingredients, a clear gel could be obtained, containing 5 wt. % PAAm-DDA polymer, 2 wt. % APG, 25 wt. % alcohol (Isopropanol:Ethanol=4:1 by volume), and deionized water.

To make the transparent coating distinguishable, 0.1 wt. % of the food dyes (FD&C blue or FD&C red) can be added into the above-mentioned formulation.

To include a sanitizing agent ($Cu'$) into the coating, 0.1 wt. % of copper acetate can be incorporated into the formulated gel. To avoid the flocculation and accelerate the dissolution, the copper acetate was first dissolved in the alcohol solvent (Isopropanol:Ethanol=4:1 by volume), which was then mixed with the PAAm-DDA/APG solution by spin-mixing (3000 rpm) for 10 mins.

Figure 4A:
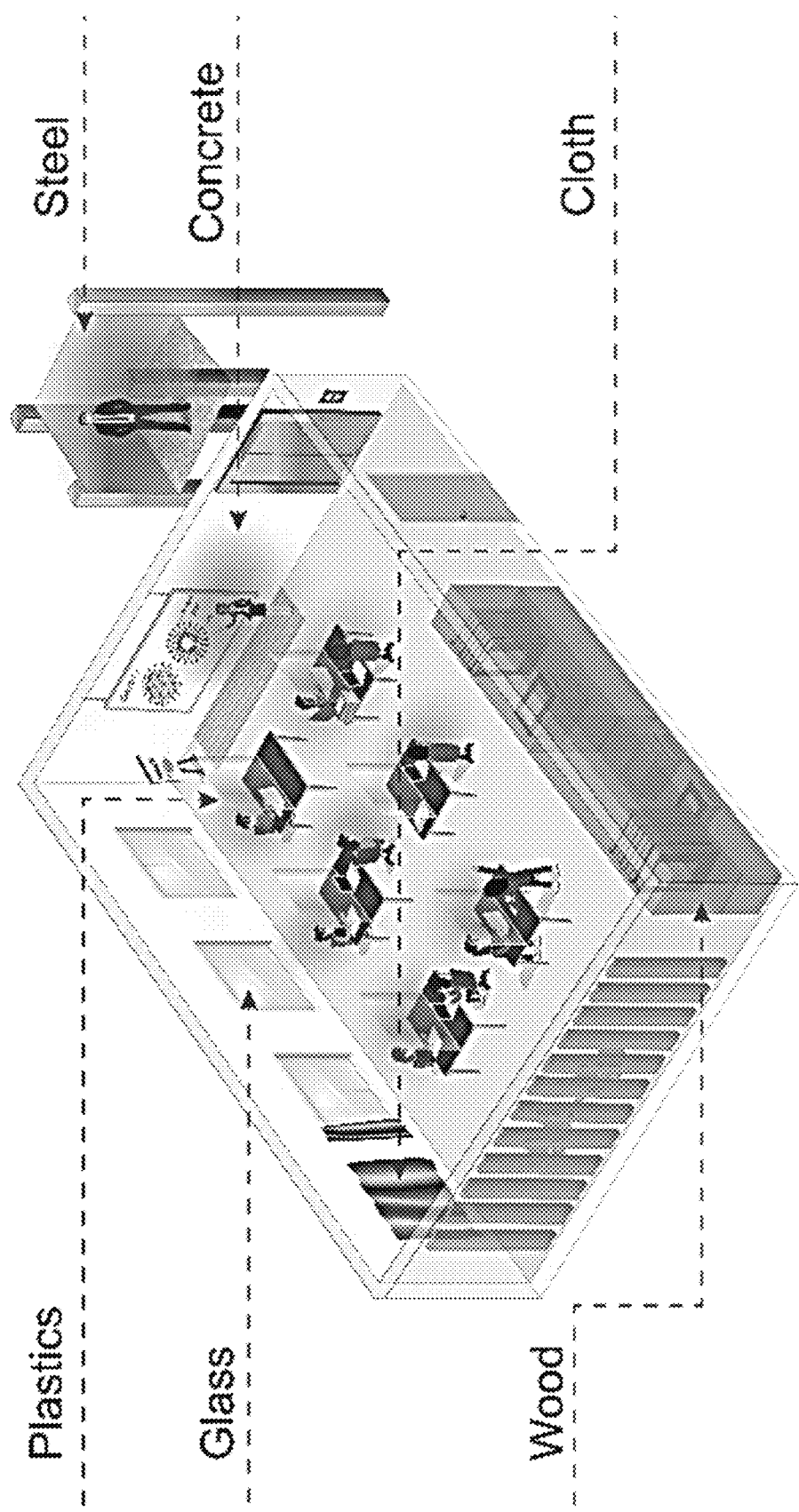

For applying coatings on common environmental surfaces shown in FIG. 4A, the colored formulated gel was directly blade-coated (on Plexiglass®) or brushed on the surfaces (window glass, wood sculpture, steel, curtain, and concrete wall), followed by natural drying overnight. Even on the vertical surfaces, the viscosity of the formulated solution was high enough to get over the gravity-induced creep.

For coating on Si collectors, the formulated solution was spin-coated on the clean Si wafer (2 cm×2 cm) at a speed of 8000 rpm for 30 s. To decrease the disturbance of dust particles, the Si wafer was pre-cleaned by being soaked in a mixture of ammonium hydroxide (28%)/hydrogen peroxide (30%)/DIW ($NH_3·H_2O/H_2O_2/H_2O$=1/1/5 in volume) for 1 hour at 80° C., followed by ultrasonic cleaning in DIW for 30 minutes and drying.

Microscopy analysis of the aerosol droplets. Size distribution of the droplet was performed. A layer of silicon oil was spread on the glass slide to seal captured aerosol droplets and slow down their evaporation. The nebulizer was placed as close as possible to the glass slide to avoid droplet evaporation as much as possible. Images were taken immediately after the aerosol stream was turned on. The process was repeated, and two images were obtained. Images of trapped droplets were then analyzed by the built-in circle Hough transform algorithm of MATLAB to recognize the droplet size. The average diameter of the droplets was found to be around 5.9 μm, which is consistent with the manufacturer's data.

In-situ observation of the droplet-substrate interaction. A transparent PET sheet or a glass slide was used as the model surface. The focal point of the microscope was adjusted to be on the top surface of the substrates. A stream of aerosol (1 wt. % NaCl solution) was generated by the hand-held nebulizer towards the top surface at an angle of ~45°. The exposure time of the CCD camera was set at 1 ms.

Aerosols capture demonstration. The detailed experimental geometry is as follows. The aerosol stream was attenuated by a mesh made of two layers of gauzes (10% of fiber density), which was then guided by a funnel into the PET tube. The stream was intentionally mis-aligned with the axis of the tube by about 15°, so that the droplets could sufficiently collide with the inner wall of the tube. A green laser beam was placed at the exit to visualize any uncaptured droplet that would scatter the laser strongly. The aerosol stream could be seen flowing through the uncoated tube. The whole process was recorded by a 30-fps camera and the videos were analyzed by using MATLAB.

2D outflow intensity map. The capture efficiency could be estimated by the 2D outflow intensity map of the scattered laser beam over time. The videos were turned into screenshots frame by frame which were then imported to MATLAB. In each of the frame, a line of one-pixel width was first drawn along the center of the laser beam near the tube exit. Every pixel on this sample line in each frame was transformed into vectors containing the relative position (0 denotes the position near the bottom of the tube, and 1 denotes the position near the top of tube) on the sample line and the brightness of each pixel (represented by the intensity value in green channel since green laser is used). Finally, a 2D outflow intensity map was plotted by integrating all the generated frame vectors over time. The color of every point in such a map denotes the relative intensity, which is shown in the color column (right y axis).

To estimate capture efficiency of the coating, the intensity of every pixel of the sample line was added up and accumulated frame by frame, followed by averaging on frame numbers. The outflow out of the uncoated tube was over an order of magnitude higher than that from the coated tube, which means over 90% of the aerosols were captured by the coating compared to the uncoated one.

Figures 3A, 3B:
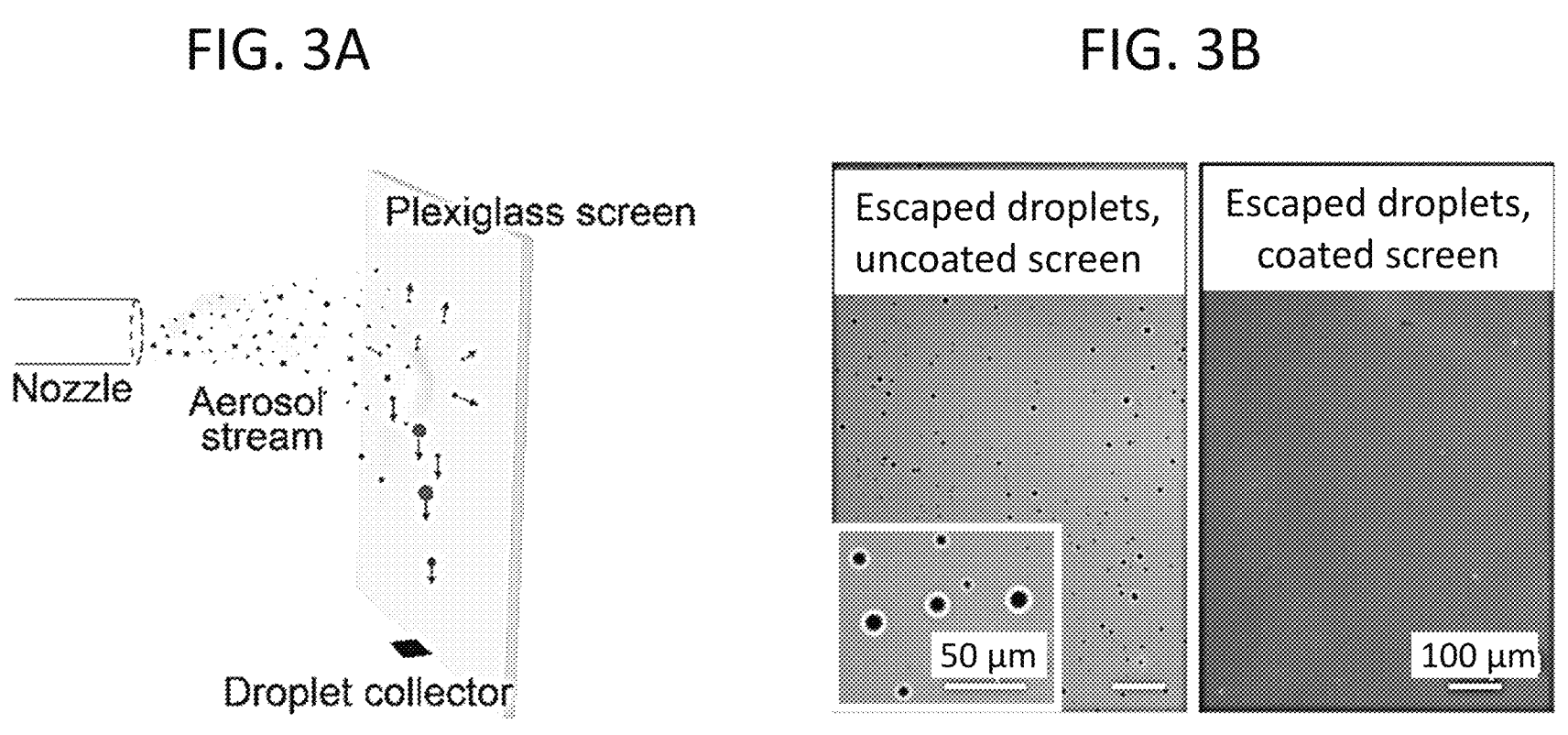

Quantitative evaluation of droplet capture in field tests. An experimental setup is shown in FIG. 3A. First, droplet collectors made of coated Si wafers were tested with lab-generated aerosols to verify the feasibility of microscopy imaging of droplet marks. A stream of attenuated aerosol generated from a nebulizer (1 wt. % NaCl) was directed towards a vertical Plexiglass® screen (30 cm×60 cm) from 5 cm away. Escaped droplets were collected by Si collectors (droplet collectors) placed at the bottom of the screen, then analyzed under microscope.

As shown in FIG. 3B, for field tests with real respiratory droplets, several volunteers loudly recited a text of their choice continuously for 30 mins, facing the center of the face shields or divider screens from about 5 cm away. The collectors were then photographed under strong oblique white light illumination, which makes large droplet highly visible as white spots. The photos were blurred and binarized to maximize the color contrast between the droplet residues and collector before being analyzed by MATLAB. The white spots were recognized and counted by the built-in imfindcircles program. Additional microscopy images were taken under bright field, reflectance mode.

Figure 2A:
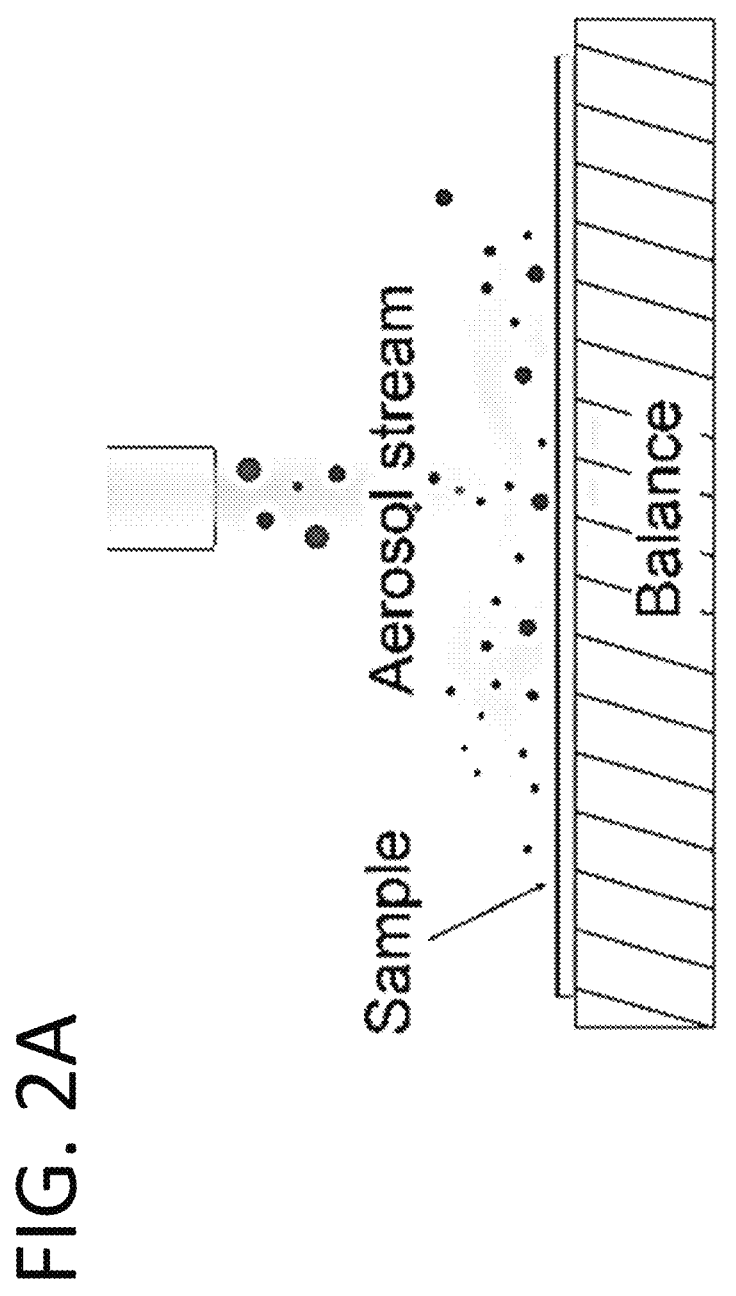
Figures 2D, 2E:
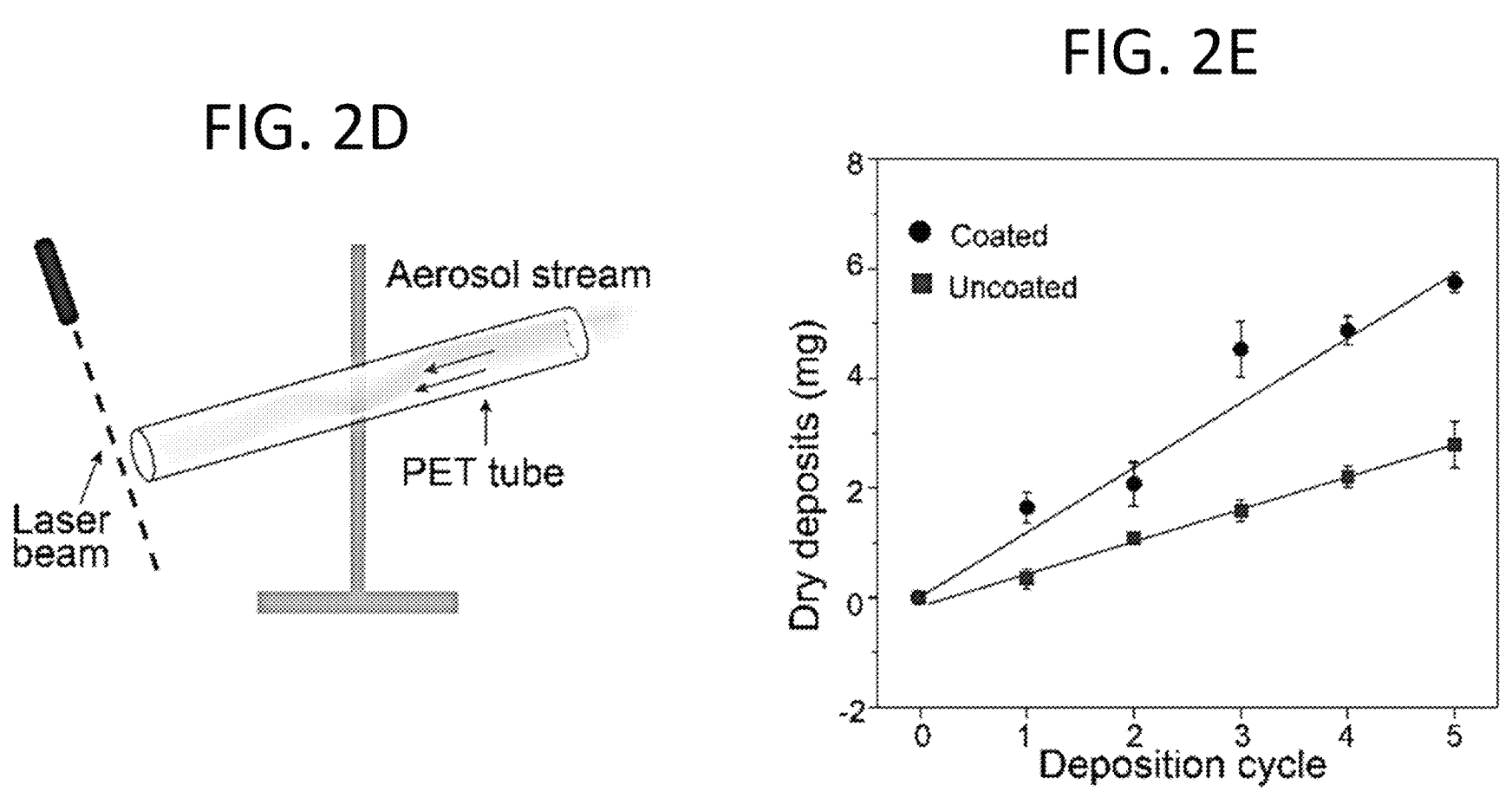

Estimation of the maximal droplet capture capacity needed in a typical workspace or public setting. FIG. 2E shows dry mass gain of the polymer coating after capturing aerosol droplets of 10 wt % NaCl. Since about 6 mg of NaCl was deposited within 5 cycles of capture, the captured droplets mass was estimated to be 60 mg. The total duration of capture was 10 minutes and the area of the sample (a fully coated glass slide, 2.5 cm×7.5 cm) was 18.75 cm². The capture rate ($Rate_I$) of the coating in the salt accumulation test shown in FIG. 2E was estimated by the following:

$$Rate_I = \frac{60 \text{ mg}}{18.75 \times 10^{-4} \text{m}^2 \times 10/60 \text{ h}} \approx 2 \times 10^5 \text{ mgm}^{-2}\text{h}^{-1}.$$

The maximal droplet capture capacity needed in a typical workspace or public setting is equal to the total amount of respiratory droplets released by people, disregarding droplet loss by evaporation and ventilation. Under a typical social-distancing arrangement (2 m between occupants), one can assume four people are allowed to occupy an office space of 5 m×4 m×2.5 m. The minimal inner surface area of the room, including the walls and the ceiling, is 65 m² (excluding the floor) without taking other surfaces into account. Assuming only less than 50% of the overall surface is suitable for coating (e.g., no-touch or low-touch surfaces), which is a drastic under-estimation, the total area of droplet-capture coating is 30 m².

Loud speech can emit 1-50 droplets per second with average droplet size of around 1 µm in diameter. For simplified calculation, 1 µm droplet was approximated as a 1 µm cube and the density of respiratory fluid was approximated to be the same as water (1 g cm⁻³), leading to a mass of $10^{-9}$ mg. Assuming the 4 people loudly talked non-stop for an hour, the total mass of released respiratory droplets in the room would be about 7×10⁻⁴ mg h⁻¹ (4×50 s⁻¹×10⁻⁹ mg×3600 s). Assuming that all of the droplets need to be captured/absorbed by the coated surfaces, the needed capture rate ($Rate_{II}$) in this room would be $$Rate_{II} = \frac{7 \times 10^{-4} \text{mg h}^{-1}}{30 \text{ m}^2} \approx 2 \times 10^{-5} \text{mg m}^{-2}\text{h}^{-1}.$$

For larger droplets (e.g., 10 µm diameter), such as those released during more violent expiratory events, the required capture rate ($Rate_{III}$) would be 2×10⁻² mg m⁻² h⁻¹.

Therefore, the droplet capture capacity of the coating shown in FIG. 2E (~10⁵ mg m⁻² h⁻¹, and far from reaching its limit) is 7-10 orders of magnitude higher than the maximal needs in practice under social-distancing arrangement (10⁻² to 10⁻⁵ mg m⁻² h⁻¹), which is not going to be saturated over extended period of time or during surges of respiratory aerosol generation.

Release of $Cu^{2+}$ from the coating. As shown in FIG. 4B, coatings about 14 µm thick were applied at the bottom surface of the wells on a microtiter plate (well diameter 2.25 cm, well depth 1.25 cm). Four wells were coated. After totally drying in a 70° C. oven, 5 mL of DIW was added to each bottom-coated hole. 3 mL of supernatant was then taken out after 5 s, 30 s, 120 s and 240 s from the four holes, respectively. Metal analysis was performed at the Northwestern University Quantitative Bio-element Imaging Center. Quantification of copper was accomplished using ICP-MS of acidified samples. Specifically, aqueous samples were acidified with concentrated trace nitric acid (>69%, Thermo Fisher Scientific, Waltham, MA, USA) to produce a final solution of 3.0% nitric acid (v/v). Quantitative standards were made using a 100 µg/mL Cu elemental standard (Inorganic Ventures, Christiansburg, VA, USA) which was used to create a 100 ng/g Cu standard in 3.0% nitric acid (v/v) in a total sample volume of 50 mL. A solution of 3.0% nitric acid was used as the calibration blank. ICP-MS was performed on a computer-controlled (QTEGRA software) Thermo iCapQ ICP-MS (Thermo Fisher Scientific, Waltham, MA, USA) operating in KED mode and equipped with an ESI SC-2DX PrepFAST autosampler (Omaha, NE, USA). Internal standard was added inline using the prepFAST system and consisted of 1 ng/mL of a mixed element solution containing Bi, In, 6Li, Sc, Tb, Y (IV-ICPMS-71D from Inorganic Ventures). Online dilution was also carried out by the prepFAST system and was used to generate a calibration curve consisting of 100, 50, 10, 2 and 1 ppb Cu. Each sample was acquired using 1 survey run (10 sweeps) and 3 main (peak jumping) runs (40 sweeps). The isotopes selected for analysis were 63,65Cu and 89Y, 115In (chosen as internal standards for data interpolation and machine stability). Instrument performance was optimized daily through auto-tuning followed by verification via a performance report (passing manufacturer specifications).

Results and Discussion

The present approach is based on removing and, in some cases, disinfecting respiratory droplets to prevent transmission of infectious diseases. The initial sizes of respiratory droplets varied greatly from sub-micron to sub-millimeter scales. Travelling droplets shrank as water evaporated but could also expand due to condensation of water vapor in humid air. Although very large droplets tend to settle quickly, under proper humidity and temperature, micron-sized droplets can stay air-borne for an extended period. As can be readily observed with aerosol droplets generated by a household humidifier, upon collision with a surface they readily bounced off and re-diffused in air (FIG. 1A). High concentration of pathogen-laden aerosols greatly increases the probability of transmission, such as when many expiratory events occur in a relatively confined, insufficiently ventilated space. If these aerosol droplets can rest on a surface, the pathogens they carry would also be trapped and easily deactivated, effectively being eliminated from the transmission pathways (FIG. 1B). Most "no-touch" or "low-touch" areas of indoor environmental surfaces in the workspace, healthcare, and public settings, such as the majority part of the walls, windows, curtains, ceilings, divider screens, surface of equipment and furniture, and elevator cars, are also exposed to respiratory aerosols. Therefore, if these surfaces are repurposed to capture respiratory droplets, they can greatly reduce air-borne infectious sources. Surface trapped pathogens can then be readily inactivated over time or by various pre-applied physical or chemical sanitization methods or during routine cleaning.

The interaction between a transparent substrate and incoming aerosol droplets can be observed in-situ using an inverted microscope. A stream of aerosol droplets from a handheld mist generator was directed toward the imaging area on the microscope slide. The sizes of the droplets were confirmed to be within 10 μm, which are in line with typical air-borne respiratory aerosols and can be readily observed under an optical microscope. Since only the droplets on or near the focal plane (i.e., top surface) can be seen, in addition to captured droplets, bouncing and gliding droplets can also be recorded in an image as they leave streaks while moving in and out of the focal plane or gliding through the imaging area within the exposure time of the camera (e.g., on the order of milli-seconds). The image in FIG. 1C represents the observation made through a clear hydrophobic polyethylene terephthalate (PET) slide, showing that the great majority of incoming droplets bounced and glided off. In contrast, after applying a coating made of poly(acrylamide-co-diallyldimethylammonium chloride (PAAm-DDA), most of the colliding droplets ended up being captured and subsequently absorbed by the coating (FIG. 1D). The trapped droplets partially dissolved the underlying polymer coating, leaving crater-like potholes after drying as shown in the laser confocal microscopy image in FIG. 1E. Note that any solute or dispersant (e.g., pathogens) in the droplets would stay in the potholes even after water evaporation, preventing them from becoming air-borne again.

In this Example, a polyelectrolyte coating was applied to modify existing surfaces, which increased its wettability and delayed the elastic recovery of deformed droplets for enhanced deposition, but also rapidly absorbed water from the captured droplets by absorption to avoid dewing. PAAm-DDA was selected as the polyelectrolyte. Droplet deposition on a PAAm-DDA modified surface can be monitored directly using a balance. As shown in FIG. 2A, a continuous stream of aerosol droplets (1 wt. % NaCl in water) was directed downward at the center of a glass substrate placed on a balance, and its mass was recorded once every 10 seconds. Coated substrates collected significantly more mass than the uncoated substrates (FIG. 2B), and the capture rate increased with coating thickness and stabilized at around 50 μm (FIG. 2C). When the aerosol stream collided with the substrate at an incident angle of θ with regard to the normal direction, the deposition rate was also found to be proportional to cos θ.

Note that the weight increase observed in FIGS. 2B-2C reflects both the capture of water droplets and absorption of water vapor in the aerosol stream. Since water vapor does not carry pathogens, it is important that the coating does enhance the capture of droplets. Leveraging different optical scattering properties of water droplets and molecular water vapor, the effect of droplet capture can be directly visualized using the experiment shown in FIG. 2D. Here, a visible stream of aerosols was passed through a slight tilted PET tube (4 cm in diameter and 30 cm in length). The stream was intentionally mis-aligned with the axis of the tube by about 15°, so that the droplets had sufficient opportunity to collide with the inner wall of the tube. A green laser beam was placed at the exit to visualize any uncaptured droplet due to their strong scattering. The aerosol stream can be seen through the entire uncoated tube, generating an apparent scattering beam at the exit in just 7 seconds, which intensified over time due to an increased flux of escaped aerosols. In contrast, the aerosol stream visibly dissipated in the coated tube, and no scattering was observed at the exit after 30 seconds. The laser beam was barely visible even after 60 seconds of aerosol injection, suggesting that the tube indeed retained most of the aerosol droplets injected. Quantitative analysis based on the intensities of the scattered laser beams suggested that the outflow out of the uncoated tube was over an order of magnitude higher than that from the coated tube, which means that the coating cut down the escaped aerosol droplets over 90%. Note that the droplet concentration in the aerosol stream used here was already many orders of magnitude higher than that of typical expiratory events, which suggests that the coating should be capable of capturing air-borne respiratory droplets continuously without being saturated.

Figure 2G:
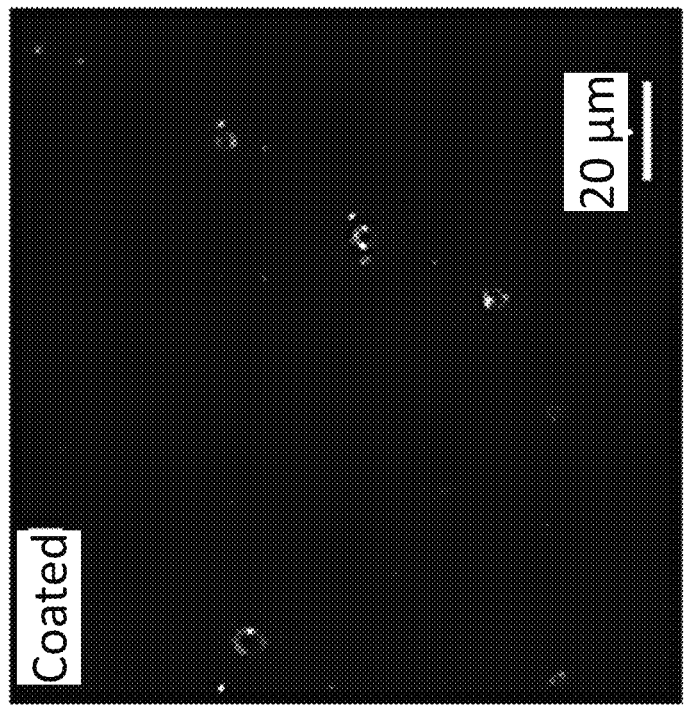
Figure 2F:
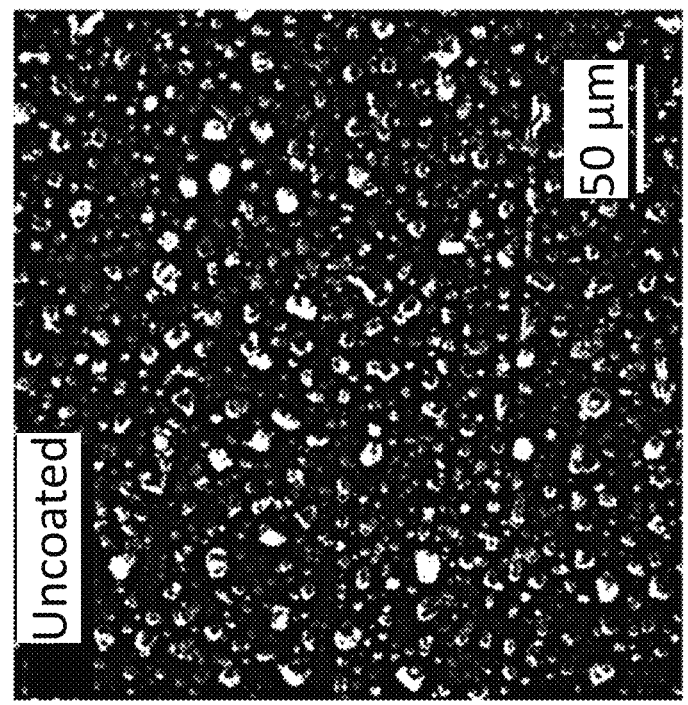

Experimental results in FIGS. 2E-2G show remarkable haze-resistant properties of the coating on transparent surfaces. An aerosol stream nebulized from a 10 wt. % of NaCl solution was guided towards a glass slide. In each cycle of deposition, the slide was exposed to the aerosol stream for 120 seconds, then dried in an oven at 60° C. to remove all absorbed water before weighing to calculate the mass of collected salt. The plots in FIG. 2E show the dry mass gain, which corresponds only to droplet deposition but not vapor absorption, on coated and uncoated glass slides after 5 cycles of salt deposition. Photos showed the appearance of the coated and uncoated sides of a slide after salt deposition. The uncoated glass slide was already hydrophilic with a contact angle of ~20°, favoring droplet retention. After drying, there was extensive deposition of micron-sized salt particles all over the surface, which acted as strong light scatterers (FIG. 2F) turning the glass slide translucent. In contrast, the coated slide was only moderately more hydrophilic with a contact angle of ~16° and collected more than twice the amount of salt. However, it remained as clear as the starting state. No scattering salt particles could be observed under the optical microscope in the dark-field reflectance mode (FIG. 2G). This was attributed to the absorption of captured droplets by the coating, which more evenly distributed the salt solution, suppressing the formation of large crystals. The coating also rendered antifogging properties as it prevented condensed water vapor or captured water droplets to bead up on the surface.

The dry mass gain results show that the rate of droplet capture by the coating was on the order of $10^5$ mg/m$^2$·h. Based on the volume of respiratory droplets released by a person during loud speaking, the maximal droplet capture capacity needed in a typical workspace or public setting is estimated to be in the range of $10^{-5}$~$10^{-2}$ mg/m$^2$ h, which is 7~10 orders of magnitude lower than the capture capacity in these experiments. To quantitatively evaluate whether the coating can indeed reduce the number of respiratory droplets escaped from environmental surfaces, collector substrates were developed to catch the escaped droplets for optical microscopy observation. The collectors were made of small silicon wafers (2 cm×2 cm), which can be attached to the edges of the surfaces to collect bounced droplets travelling towards their directions (FIG. 3A). The silicon wafers were spin-coated with the formulated gel to better trap escaped droplets. In this case, the optimal thickness of the coating was found to be around 75 μm, which produced the best contrast of the crater marks by the caught droplets under reflectance mode. The function of the collectors was first tested using a slightly attenuated, lab-generated, horizontal aerosol stream, which was directed towards the center of a vertically placed Plexiglass® screen 5 cm away for 5 minutes. Microscopy observation of the collectors placed at the middle of the lower edge from an uncoated and a coated Plexiglass® screen revealed a drastic difference in the number of escaped aerosol droplets. Numerous droplet marks were observed on the collector attached to the uncoated screen (FIG. 3B, left), while barely any can be seen on the one attached to the coated screen (FIG. 3B, right).

Figure 3C:
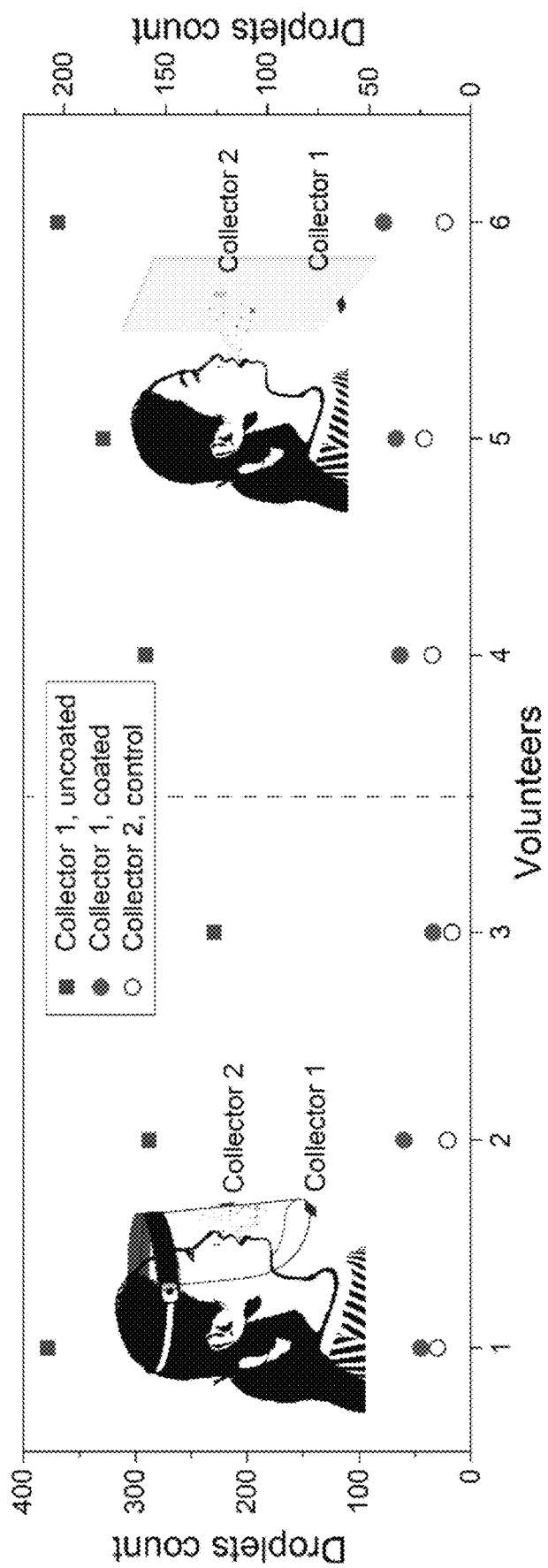

The concentration of expiratory droplets released by a human is many orders of magnitude lower than those of lab-generated aerosol droplets. They also have much broader size distribution and contain many large sub-millimeter sized droplets, which tend to splash and break up into smaller ones upon colliding with a surface. Therefore, a field test was performed to examine the droplet-capturing performance of the coating with real respiratory droplets released during loud reciting, where droplets bouncing, trapping, spreading, and splashing were all convoluted together. The coating was applied to PET face shields (33 cm×27 cm) (FIG. 3C, left inset) and Plexiglass® divider screens (30 cm×60 cm) (FIG. 3C, right inset). Several volunteers loudly recited a text of their choice continuously for 30 mins, facing the center of the shields and screens from about 5 cm away. Since most of the escaped droplets traveled downwards, one set of collectors was placed at the center of the bottom edge to catch escaped respiratory droplets. Another set was placed on the outer surfaces, where no droplets were expected, as a blank control to account for features (e.g., pinholes in the spin-coated coatings or near-spherical dust particles) that are indistinguishable from droplet marks. Collectors placed at side and top edges did not collect a significant number of droplets, and thus are not shown in the drawings. As shown in FIG. 3C, although the number of released and escaped droplets from uncoated surfaces varied by person, the coated surfaces consistently reduced the number of escaped droplets close to the level of the blank control. A similar trend was observed with the Plexiglass® screen. It is worth noting that in addition to capturing small respiratory aerosol droplets, the coatings were also capable of drastically reducing the number of escaped large, sub-micron sized droplets. These large droplets escape by breaking apart and splashing off a surface. Therefore, the coating offers a comprehensive droplet retention solution that prevents small droplets from bouncing off and large ones from splashing.

For practical purposes, droplet-capturing coatings should be safe to use, easy to formulate, non-destructive and yet readily applicable to a broad range of common environmental surfaces of different material compositions, wettability, and textures. The coating demonstrated so far is highly transparent and resistant to fogging and hazing, which works well on transparent surfaces. But it would also be very useful to make it colored for labelling, warning, therapeutic, psychological, and aesthetic purposes, and tolerant to other additives to render new functions. All these properties have been achieved using an optimized formulation based on PAAm-DDA and alkyl polyglycosides (APG), a biodegradable non-ionic surfactant in water-alcohol mixture. APG acts as a viscosity modifier and helps to accommodate ionic and colloidal additives to make homogeneous coating solutions, and significantly improves the wettability of the coating solution on different surfaces, making the coating agnostic to indoor environmental surfaces in the workplace, healthcare, elderly care, and public settings (FIG. 4A), where accumulation of respiratory droplets is mostly likely to occur. A few examples are illustrated in FIG. 4A, including a Plexiglass® divider screen, which has become ubiquitous to block the direct exchange of respiratory droplets between people, a glass window, a wooden structure with complex geometry, a stainless-steel frame with decorative features, a rough concrete wall, and a microfiber cloth curtain. The high transparency of the coatings makes them visually indistinguishable; therefore, food dyes (e.g., 0.1 wt. % FD&C blue or FD&C red) were added to the formulation to make the coatings visible. The colored formulation was applied to these surfaces without the need for extensive pre-cleaning or chemical treatment, and it still yielded conformal and uniform coatings.

To accelerate the disinfection of the captured droplets and the pathogens, broad-spectrum sanitization agents, such as $Cu^{2+}$, can be incorporated in the coating, too, without altering the transparency or the processability of the formulation. Droplets caught on the coating can swell and partially dissolve the coating, thus extracting $Cu^{2+}$ to interact with any pathogen particles that may be present in the droplets. The release of $Cu^{2+}$ was studied by inductively coupled plasma (ICP) analysis (FIG. 4B), which was found to approximate Fick's first diffusion law. Since $Cu^{2+}$ can diffuse into water in any captured droplets, as well as within the swollen coating, it should lead to accelerated inaction of pathogens trapped on the surface.

CONCLUSION

Regardless of the nature of the pathogens, preventing infectious respiratory droplets from reaching the respiratory tracts of others is the foundation of public health responses and disease control measures. The majority of areas of indoor environmental surfaces are barely or would not be touched, and thus readily available to be repurposed as a passive, low-cost, high capacity, and long-lasting tool for respiratory droplet removal without increasing fomite infection. The coating demonstrated here is effective for droplet capture over a broad range of droplet sizes and concentrations. The coating formulation is based on benign solvents and inexpensive cosmetic ingredients. It is highly tolerant to additional components for achieving new functions including coloration and sanitization. Therefore, it is already scalable for coating large areas of environmental surfaces regardless of their material compositions, wettability, geometries and textures, with additional advantages including fog- and haze-resistance, which is ideal for transparent surfaces. The coating also offers a drop-in enhancement of the intended functions of face shields and divider screens. However, in the context of enhancing preparedness for future outbreaks of infectious respiratory diseases, droplet-capture coating helps to reduce air-borne droplets that are most difficult to manage, which could become a useful addition to current public health measures including the practice of isolation, social distancing, and the use of masks, face shields, and divider screens.

Additional information may be found in U.S. Patent Application No. 63/168,889, which is hereby incorporated by reference in its entirety.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

All numeric values of parameters in the present disclosure are proceeded by the term "about" which means approximately. This encompasses those variations inherent to the measurement of the relevant parameter as understood by those of ordinary skill in the art. This also encompasses the exact value of the disclosed numeric value and values that round to the disclosed numeric value.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method of capturing respiratory droplets, the method comprising absorbing respiratory droplets on a surface of a coating, the coating comprising a polyelectrolyte polymer and a viscosity modifier, wherein absorbed droplets leave depressions in the surface of the coating.

2. The method of claim 1, wherein the respiratory droplets are those exhaled from breath of a mammalian subject.

3. The method of claim 1, wherein the coating exhibits a capture rate of at least $10^2$ mg/m$^2$h.

4. The method of claim 1, wherein the coating has a thickness corresponding to a peak in a plot of capture rate versus thickness for the coating.

5. The method of claim 1, wherein the coating has a thickness in a range of from 30 μm to 60 μm.

6. The method of claim 1, wherein the polyelectrolyte polymer and the viscosity modifier are present in the coating at a weight ratio in a range of from 3:1 to 2:1.

7. The method of claim 1, wherein the polyelectrolyte polymer is a poly(acrylamide-co-diallyldialkylammonium salt) and the viscosity modifier is an alkyl polyglycoside.

8. The method of claim 1, wherein the coating further comprises a colorant, an anti-pathogen agent, or a combination thereof.

9. The method of claim 1, wherein the coating consists of the polyelectrolyte polymer, the viscosity modifier, and optionally, one or both of a colorant and an anti-pathogen agent.

10. The method of claim 1, wherein the coating consists of the polyelectrolyte polymer and the viscosity modifier.

11. The method of claim 1, wherein the polyelectrolyte polymer and the viscosity modifier are present in the coating at a weight ratio in a range of from 3:1 to 2:1; the coating has a thickness in a range of from 30 μm to 60 μm; and wherein the polyelectrolyte polymer is a poly(acrylamide-co-diallyldialkylammonium salt) and the viscosity modifier is an alkyl polyglycoside.

12. The method of claim 11, wherein the coating consists of the polyelectrolyte polymer, the viscosity modifier, and optionally, one or both of a colorant and an anti-pathogen agent.

13. The method of claim 11, wherein the coating consists of the polyelectrolyte polymer and the viscosity modifier.

14. The method of claim 1, further comprising forming the coating by applying a coating composition comprising the polyelectrolyte polymer, the viscosity modifier, and a solvent on a substrate.

15. The method of claim 1, further comprising placing the coating in an atmosphere comprising the respiratory droplets.

* * * * *